United States Patent
Reach, Jr.

(10) Patent No.: US 9,351,778 B2
(45) Date of Patent: May 31, 2016

(54) POROUS EXPANSION BOLT

(75) Inventor: John S. Reach, Jr., Guilford, CT (US)

(73) Assignee: YALE UNIVERSITY, New Haven, CT (US)

( * ) Notice: Subject to any disclaimer, the term of this patent is extended or adjusted under 35 U.S.C. 154(b) by 270 days.

(21) Appl. No.: 12/992,682

(22) PCT Filed: Jun. 19, 2009

(86) PCT No.: PCT/US2009/003676
§ 371 (c)(1),
(2), (4) Date: Nov. 15, 2010

(87) PCT Pub. No.: WO2009/154781
PCT Pub. Date: Dec. 23, 2009

(65) Prior Publication Data
US 2011/0071579 A1  Mar. 24, 2011

Related U.S. Application Data (60) Provisional application No. 61/074,204, filed on Jun. 20, 2008.

(51) Int. Cl.
*A61B 17/68* (2006.01)
*A61B 17/56* (2006.01)
(Continued)

(52) U.S. Cl.
CPC .............. *A61B 17/84* (2013.01); *A61B 17/0401* (2013.01); *A61F 2/0811* (2013.01);
(Continued)

(58) Field of Classification Search
CPC .. A61B 17/04; A61B 17/0401; A61B 17/844; A61B 17/864; A61B 17/8665; A61B 17/8685; A61B 2017/0404; A61B 2017/0408; A61B 2017/0412; A61B 2017/0414; A61B 2017/042; A61B 2017/0424; A61B 2017/0425; A61B 2017/0247; A61B 2017/0429; A61B 2017/043; A61B 2017/0432; A61B 2017/0433; A61B 2017/0435; A61B 2017/0438; A61B 2017/044; A61B 2017/0443; A61B 2017/0445; A61B 2017/0451; A61B 2017/8655; A61B 2017/867; A61B 2017/8675; Y10T 29/49948; F16B 29/00; F16B 13/04; F16B 13/045; F16B 13/06; F16B 13/063; F16B 13/068; F16B 13/0841; F16B 13/0858; F16B 13/0883
USPC ......... 606/301, 302, 304, 305, 307, 308, 313, 606/314, 323, 326, 327, 328, 331, 232; 411/57.1, 58, 60.1, 60.2, 55, 24, 27, 411/49, 32, 33, 80.1, 80.2, 80.5, 80.6
See application file for complete search history.

(56) References Cited

U.S. PATENT DOCUMENTS

| | | | | |
|---|---|---|---|---|
| 3,974,734 | A | * | 8/1976 | Machtle ........................ 411/26 |
| 4,011,602 | A | * | 3/1977 | Rybicki et al. ............. 623/23.76 |
| 4,655,462 | A | * | 4/1987 | Balsells ....................... 267/167 |
| 5,282,861 | A | * | 2/1994 | Kaplan ...................... 623/23.51 |
| 5,464,427 | A |   | 11/1995 | Curtis et al. |

(Continued)

OTHER PUBLICATIONS

Whang K., Tsai D.C., Nam E.K., Aitken M., Sprague S.M., Patel P.K., Healy K.E. (1998) "Ectopic bone formation via rhBMP-2 delivery from porous bioabsorbable polymer scaffolds". Journal of Biomedical Materials Research. 42(4): 491-499.*

*Primary Examiner* — Kevin T Truong
*Assistant Examiner* — Tracy Kamikawa
(74) *Attorney, Agent, or Firm* — Welsh Flaxman & Gitler LLC (57) ABSTRACT

A biocompatible expansion bolt includes a central screw and an expansion shell positioned about the central screw. The expansion shell is shaped and dimensioned for controlled expansion between a first diameter and a larger, second diameter, wherein the expansion shell is composed of porous material allowing for tissue in-growth.

8 Claims, 11 Drawing Sheets

(51) Int. Cl.
*A61B 17/84* (2006.01)
*A61B 17/04* (2006.01)
*A61F 2/42* (2006.01)
*A61F 2/08* (2006.01)
*A61B 17/72* (2006.01)
*A61B 17/88* (2006.01)

(52) U.S. Cl.
CPC ........... *A61F2/4202* (2013.01); *A61B 17/7258* (2013.01); *A61B 17/8875* (2013.01); *A61B 2017/0433* (2013.01); *A61B 2017/0441* (2013.01); *A61F 2002/0823* (2013.01); *A61F 2002/0829* (2013.01); *A61F 2002/0835* (2013.01); *A61F 2002/0858* (2013.01); *A61F 2002/0888* (2013.01); *A61F 2002/4223* (2013.01)

(56) References Cited

U.S. PATENT DOCUMENTS

| | | | |
|---|---|---|---|
| 5,725,529 A * | 3/1998 | Nicholson et al. | 606/232 |
| 5,766,255 A | 6/1998 | Slamin et al. | |
| 5,782,865 A * | 7/1998 | Grotz | 606/232 |
| 6,276,883 B1 | 8/2001 | Unsworth et al. | |
| 6,357,960 B1 * | 3/2002 | Cornelius et al. | 403/381 |
| 2001/0053913 A1 | 12/2001 | Freedland et al. | |
| 2006/0149269 A1 * | 7/2006 | Kertzner et al. | 606/80 |
| 2006/0235410 A1 | 10/2006 | Ralph et al. | |
| 2007/0162022 A1 * | 7/2007 | Zhang et al. | 606/72 |
| 2008/0195099 A1 * | 8/2008 | Minas | 606/70 |
| 2008/0208264 A1 * | 8/2008 | Lazarof | 606/310 |
| 2008/0221624 A1 * | 9/2008 | Gooch | 606/302 |
| 2009/0043342 A1 * | 2/2009 | Freedland | 606/313 |

* cited by examiner

POROUS EXPANSION BOLT

CROSS REFERENCE TO RELATED APPLICATIONS

This application is the national phase of PCT/US2009/003676, filed Jun. 19, 2009, entitled "POROUS METAL EXPANSION BOLT" which claims the benefit of U.S. Provisional Patent Application Ser. No. 61/074,204, filed Jun. 20, 2008, entitled "POROUS METAL EXPANSION BOLT".

BACKGROUND OF THE INVENTION

1. Field of the Invention

The invention relates to medical devices. Specifically, the invention relates to a porous metal expansion bolt for use in surgical procedures and the fixation and biologic integration of various tissues.

2. Description of the Related Art

Connective tissue fixation devices for securing tendon, ligament and bone to other connective tissues are typically fabricated from medically approved metallic or biodegradable materials. Although generally successful in achieving the goal of temporary mechanical fixation of graft tissue to target tissue, currently available connective tissue fixation devices have a number of well-known disadvantages.

A universal limitation to all currently described soft-tissue fixation devices is that ultimate biologic integration of tendon, ligament, and bone through in-growth healing occurs solely on the biologic side of the interface. No soft-tissue integration has ever been shown to be sustained directly to the implant, which, by all current designs, must occupy a substantial portion of the area available for graft-target tissue healing. This lack of in-growth area limits initial and ultimate strength of construct. In addition, the ability of the connective tissue to respond to future damage and functional remodeling is limited when fixation is achieved mechanically.

Biodegradable (or bio-absorbable) fixation systems have numerous well documented problems. These implants are brittle and may fail upon initial implantation, they may degrade rapidly and unpredictably with loss of fixation strength, and they may produce local and systemic host reactions leading to the rejection of the implant, catastrophic failure, and massive bone loss. An additional disadvantage of a current interference screw design is difficulty of screw removal in cases that require such hardware removal. In the case of bio-absorbable implants, frequently structural competency is lost and the fixation device breaks deep with in the host tissue; in the case of metallic implants, soft-tissue damage can occur when the threads re-engage the tenuous collagen structures. Interference screw tissue implants commonly may include a threaded shank joined to an enlarged head having a transverse slot, hexagonal, or star-shaped driver for advancing the screw into the bone. The enlarged heads or prominent variable pitch diameters on such screws may protrude from the implantation site resulting in chronic irritation, inflammation of surrounding body tissue, and early or late reconstruction failure.

When placed, as is common, in proximity to repetitively moveable joints, such medical screw fixation devices may, in certain instances, cause abrading of ligaments, tendons, nerves, arteries, veins, bone, cartilage, and skin during the normal physiologic motion of the joint. Fixation implants may back out after insertion, protruding into surrounding tissue and causing discomfort and morbidity.

Furthermore, due to a phenomenon known as "stress shielding," fixation implants which do not closely match the elastic modulus (flexibility) of the surrounding host tissue may shield this connective tissue (bone, tendon, ligament) from beneficial stresses that enhance healing. It has been shown that moderate periodic stress on bone tissue, such as the stress produced by exercise, helps prevent decalcification and loss of the bone. Under these physiologic conditions, the stress shielding which results from the long-term use of implant-host modulus mismatch fixation devices can lead to osteoporosis, tissue weakness, and catastrophic failure.

SUMMARY OF THE INVENTION

It is, therefore, an object of the present invention to provide a biocompatible expansion bolt including a central screw and an expansion shell positioned about the central screw. The expansion shell is shaped and dimensioned for controlled expansion between a first diameter and a larger, second diameter, wherein the expansion shell is composed of porous material allowing for tissue in-growth.

It is also an object of the present invention to provide an expansion bolt wherein the porous material is elemental metal tantalum.

It is another object of the present invention to provide an expansion bolt wherein the porous material is selected from the group consisting of elemental metal tantalum, porous titanium, porous cobalt chrome, porous aluminum, porous stainless steel, and porous ceramics.

It is a further object of the present invention to provide an expansion bolt including a suture attachment loop.

It is also an object of the present invention to provide an expansion bolt wherein the central screw includes the suture attachment loop.

It is another object of the present invention to provide an expansion bolt wherein the expansion shell includes the suture attachment loop.

It is a further object of the present invention to provide an expansion bolt wherein the expansion shell is composed of the plurality of expansion members.

It is also an object of the present invention to provide an expansion bolt wherein the expansion members are constrained by a lattice structure.

It is another object of the present invention to provide an expansion bolt wherein the lattice structure is a coiled spring.

It is also an object of the present invention to provide a method for tissue attachment including forming a cavity in a bone structure, positioning tissue within the cavity and deploying an expansion bolt within the cavity. The expansion bolt includes a central screw and an expansion shell positioned about the central screw, the expansion shell being shaped and dimensioned for controlled continually variable expansion between a first diameter and a larger, second diameter, wherein the expansion shell is composed of porous material allowing for tissue in-growth. The expansion shell is then expanded to the second diameter pushing the expansion shell outwardly and into contact with the tissue pressing the tissue between the wall of the cavity and the expansion shell.

It is a further object of the present invention to provide a method wherein the tissue is a tendon.

It is also an object of the present invention to provide a method wherein the tissue is ligament.

It is another object of the present invention to provide a method wherein the expansion bolt is expanded to apply a pressure of between approximately 0.25 inch-pounds and approximately 16 inch-pounds.

It is a further object of the present invention to provide a method wherein the expansion bolt is expanded to apply a pressure of approximately 8 inch-pounds.

It is also an object of the present invention to provide a method wherein the step of expanding includes allowing for tissue creep.

It is another object of the present invention to provide a method for bone void filling including the steps of forming a cavity across adjacent bone structures and deploying an expansion bolt within the cavity and across the bone structures. The expansion bolt includes a central screw and an expansion shell positioned about the central screw, the expansion shell being shaped and dimensioned for controlled and continuously variable expansion between a first diameter and a larger, second diameter, wherein the expansion shell is composed of porous material allowing for tissue in-growth. The expansion shell is expanded to the second diameter pushing the expansion shell outwardly and into contact with the bone structures for securing the expansion bolt in position within the cavity.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

In accordance with the present invention, and with reference to the embodiment shown in FIGS. 1 to 7A-D, an interference expansion bolt 10 composed of biocompatible, porous material that allows tissue integration is disclosed. The present expansion bolt 10 provides a mechanism for achieving the optimal milieu for connective tissue fixation through the biologic tissue integration both into the target tissue as well as into the expansion bolt 10 itself. As is discussed below in greater detail, the present expansion bolt 10 optimizes tissue integration through design, technique, and material. As will be appreciated based upon the following disclosure, the present expansion bolt 10 allows multiple functions including, but not limited to, arthroereisis, biotenodesis, interference screw, suture anchor, bone void filler, implant fixation system, arthrodesis.

Figure 1:
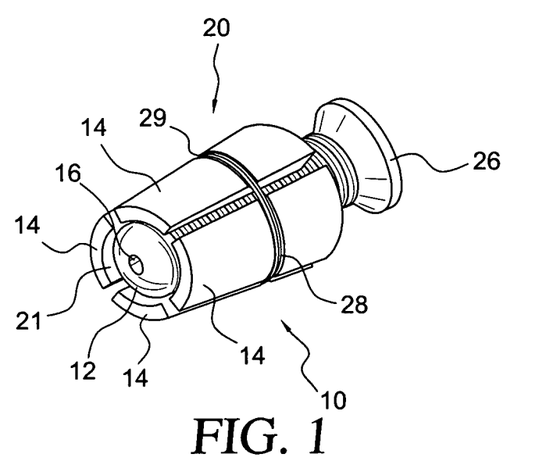
FIG. 1 is a perspective view of an expansion bolt in accordance with a first embodiment.
Figure 2:
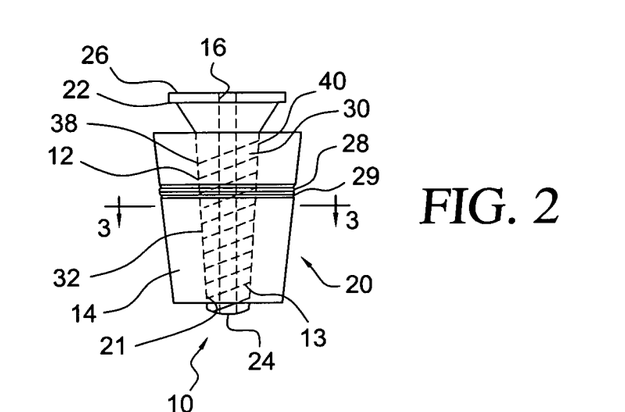
FIG. 2 is a side view of the expansion bolt shown in FIG. 1.
Figure 3:
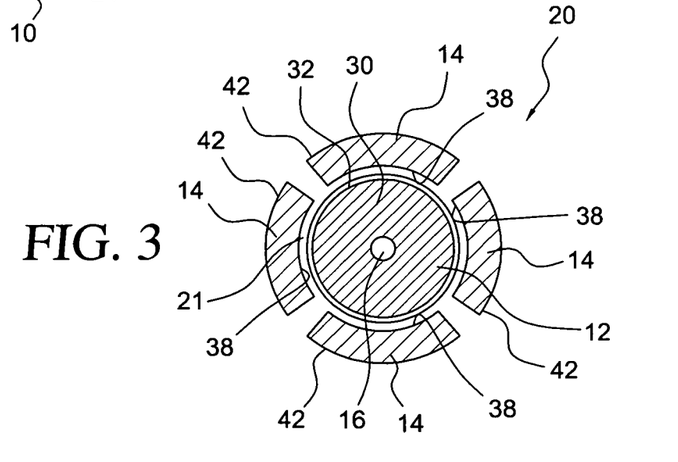
FIG. 3 is a cross sectional view of the expansion bolt shown in FIG. 1 along the line 3-3 in FIG. 2.
Figure 4A:
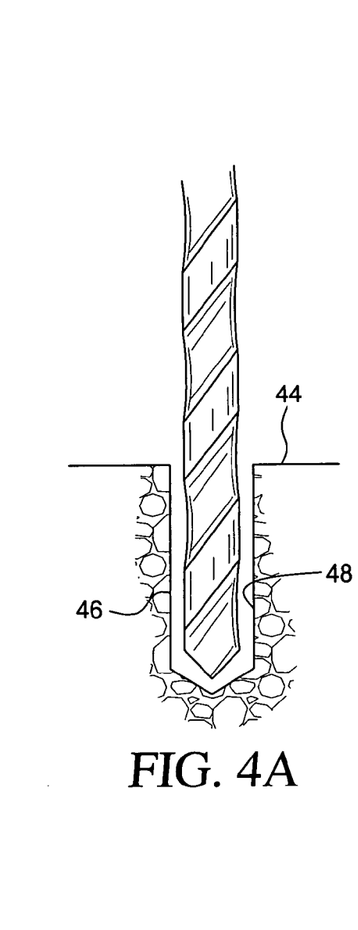
FIGS. 4A-D show the steps in using the expansion bolt shown in FIGS. 1-3 for securing a tendon.
Figure 4B:
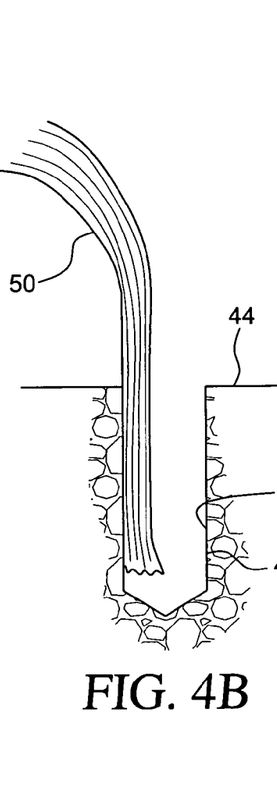
Figure 4C:
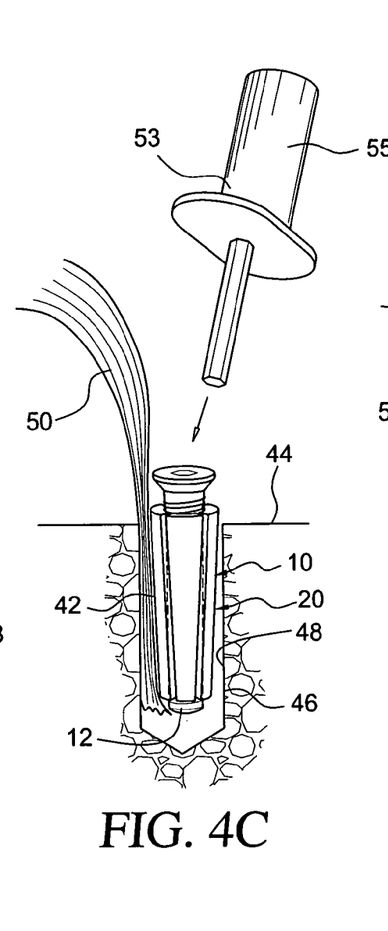
Figure 4D:
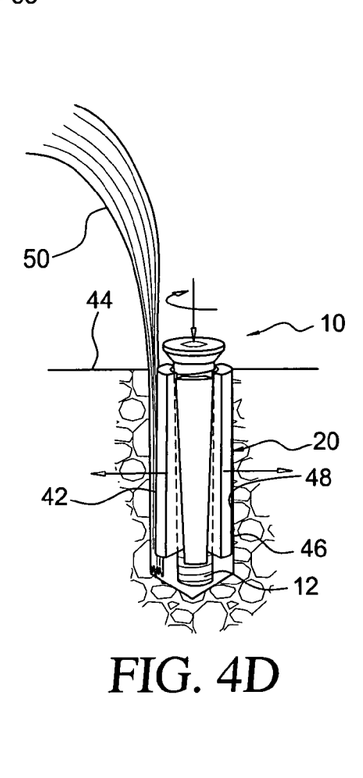
Figure 5A:
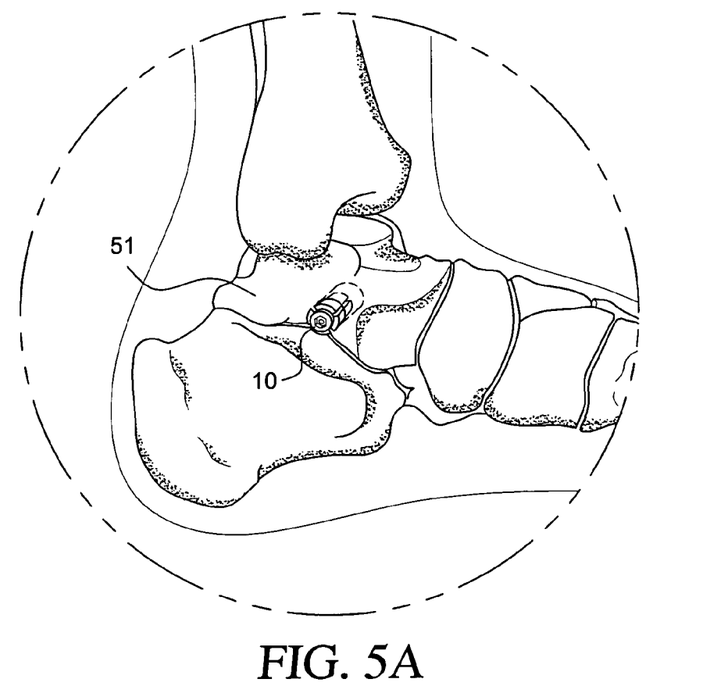
FIGS. 5A-D show the steps in using the expansion bolt shown in FIGS. 1-3 for an arthroereisis procedure.
Figure 5B:
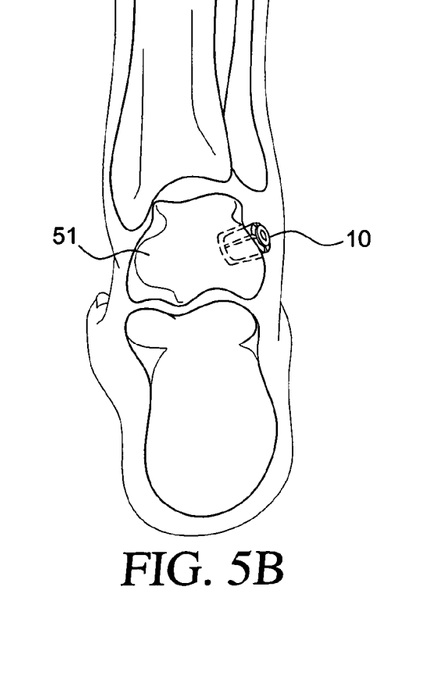
Figure 5C:
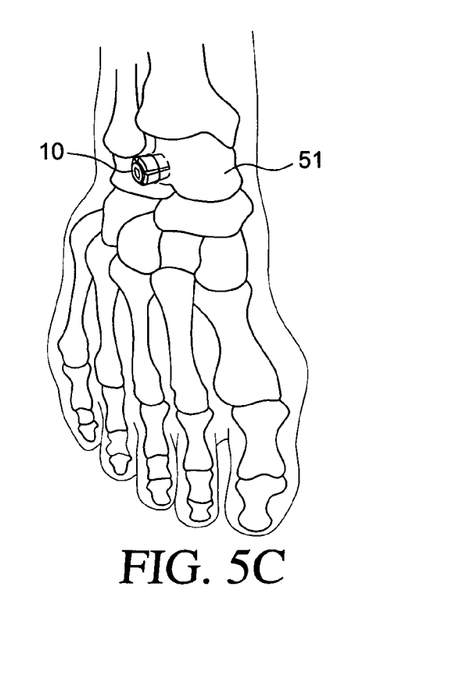
Figure 5D:
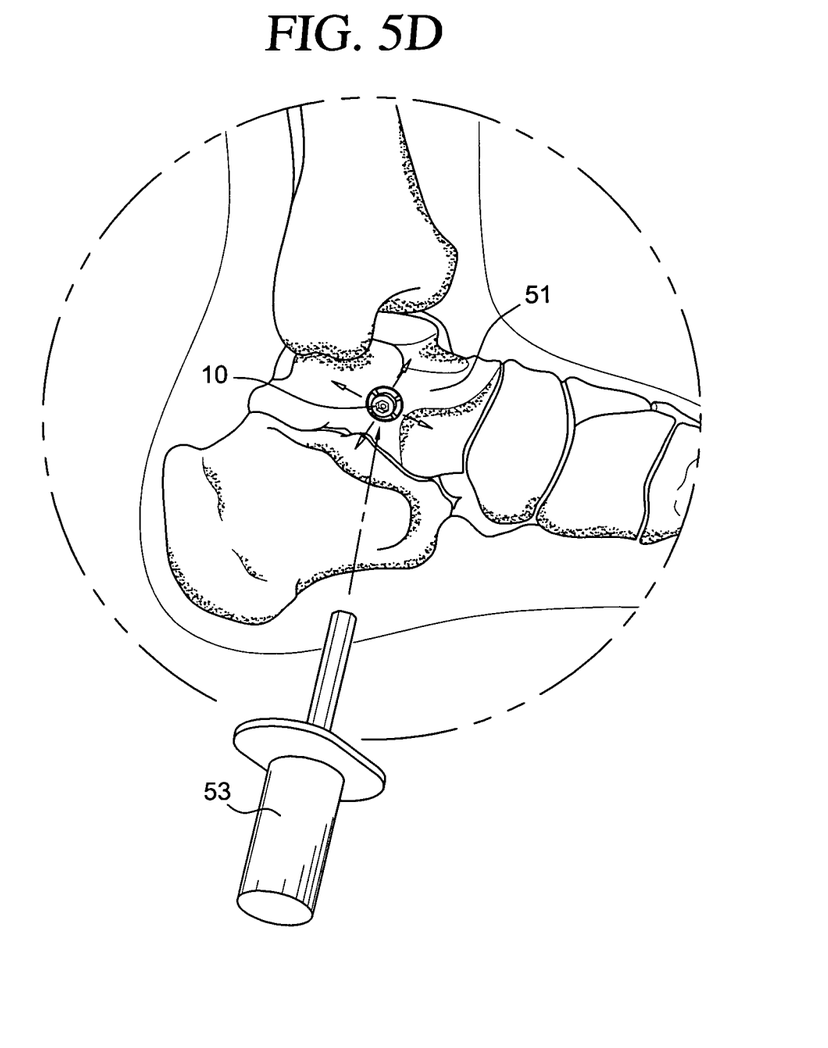
Figure 6A:
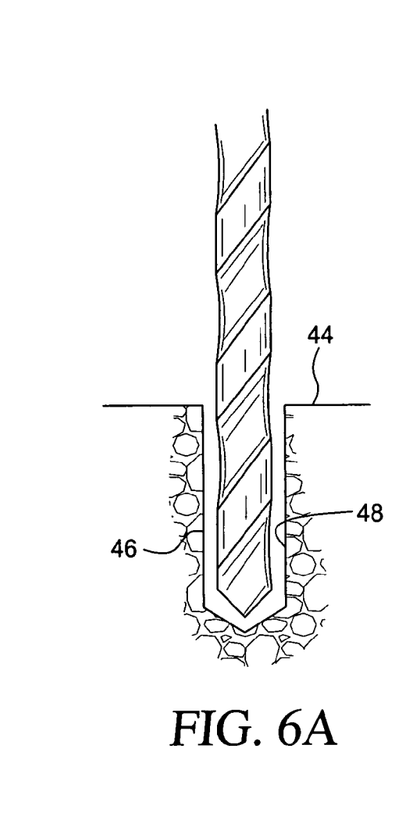
FIGS. 6A-D show the steps in using the expansion bolt shown in FIGS. 1-3 as a suture anchor.
Figure 6B:
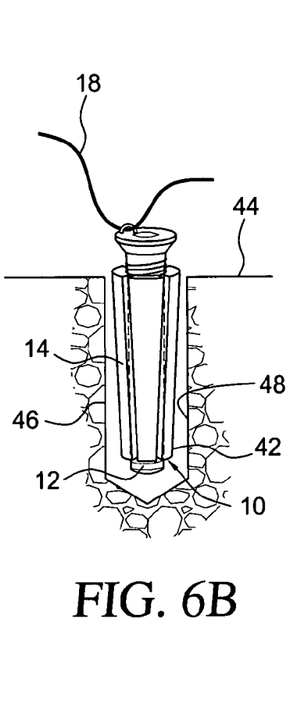
Figure 6C:
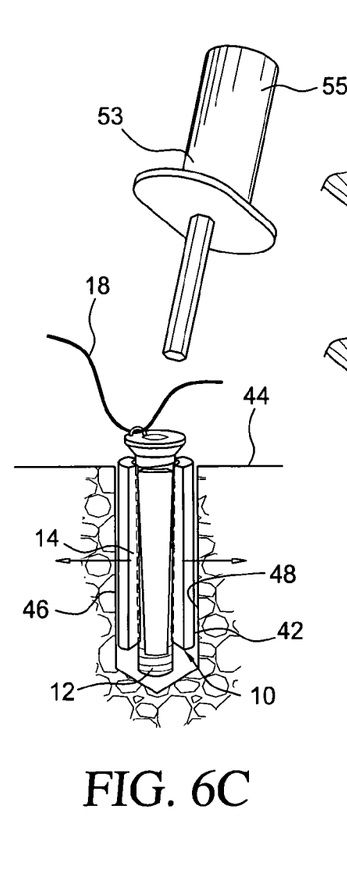
Figure 6D:
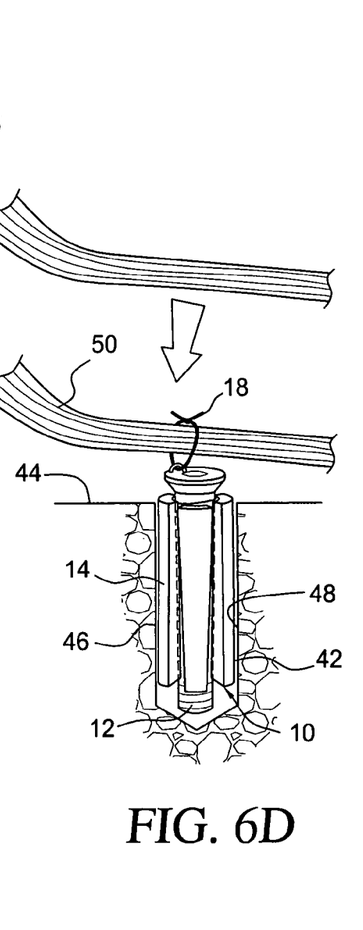

In accordance with a first embodiment, in particular, with reference to FIGS. 1 to 3, the present interference expansion bolt 10 has a conical, selectively removable retention member composed of a threaded central screw 12 having a longitudinally extending shaft, a substantially helical groove 13 being formed on the central screw 12 and extending longitudinal thereon. The central screw 12 functions to cause radial expansion of the outer diameter of the expansion bolt 10 to widen the outer diameter thereof as the central screw 12 is driven forward.

As the various embodiments disclosed below show, the present expansion bolt 10 may be provided with various attachment points within and on each major subcomponent thereof which allow the addition of a suture 18 (or plurality of tissue affixing materials: e.g. endobutton) to the expansion bolt 10. The exterior of the expansion bolt 10 implant is fabricated of a foam (also known as, porous or trabecualar) expansion shell 20 that is constrained within an expandable holding lattice structure 28. The present expansion bolt 10 functions by (1) first being deployed into the target area in its small first diameter form; (2) and progressively being expanded to a continually adjustable second diameter (larger than the first diameter) until the appropriate amount of "hoop stress" pressure is generated between the expansion bolt 10 and the target area for optimal tissue in-growth. Where it is desired to use the expansion bolt for securing tissue to the target area, the tissue is positioned between the expansion bolt 10 and the target area such that it is frictionally held in position as a result of the "hoop stress" applied by the expansion bolt 10. Initial fixation may be achieved through the various attachment points within and on the major subcomponents of the expansion bolt 10. In accordance with a preferred embodiment, the pressure is controlled through the use of a torque wrench (or other torque applying delivery tool) and the applied pressure is preferably between approximately 0.25 inch·pounds and approximately 16 inch·pounds, more preferably, approximately 8 inch·pounds. The controlled applied pressure used in accordance with a preferred embodiment of the present invention has been determined to achieve rapid and biologic tissue in-growth fixation. Once deployed and radially expanded to its second diameter, it is intended that the expansion screw 10 be then left in place for tissue integration.

Using a controlled hoop-stress compression mechanism, the amount of pressure exerted by the foam (porous, trabecular) expansion shell 20 of the expansion bolt 10 toward the graft and target tissue is proportional to the polar moment of inertia applied by a torque wrench (with a tapping head) 53 (or other tool used for gripping, turning, twisting or expanding objects under a reproducible index unit of force). Thus the optimal mechanical stimulus of bone (under. Wolff's Law) and tendon and ligament is generated. The expansile design of the expansion bolt 10 allows a single expansion bolt 10 to function over a range of implant sizes, affording decreased inventory, surgical manipulation, operative time and enhanced placement and removal facility.

As will be discussed below in greater detail, the present interference expansion bolt 10 is composed of biocompatible, porous material that allows tissue integration while the tissue is held in position by the present expansion bolt 10 through the application of a hoop-stress compression mechanism. The interference expansion bolt 10 allows both fixation and biologic in-growth of tendon, ligament, bone and other connective tissues. The expansion bolt 10 may be manufactured in a variety of sizes to allow for versatility in the use thereof. This allows for a decrease in inventory, surgical manipulation, and operative time. It is contemplated the present interference expansion bolt 10 has many potential applications, including but not limited to, use as an arthroereisis implant, a biotenodesis or interference screw, a suture anchor, a bone void filler, an implant fixation system (stem, outer shell) and an arthrodesis implant.

Highly porous materials have shown promise for bone in-growth applications. Porous metals, also known as foams, can be produced with interconnective porosity coupled with a regular pore shape and size. One such material that is commercially available, and is appropriate for use in accordance with the present invention, is composed of elemental metal tantalum fabricated with interconnective porosity with use of a metal vapor deposition technique. This material is currently sold under the tradename TRABECULAR metal by Zimmer of Warsaw, Ind. However, and as is discussed below in greater detail, other porous materials may be employed without departing from the spirit of the present invention. For example, it is contemplated that porous titanium, for example, REGENEREX as manufactured and sold by Biomet Inc. or TRITANIUM DIMENSIONAL METAL as manufactured and sold by Stryker, Inc., porous cobalt chrome, porous aluminum, porous stainless steel, BIOFOAM (such as manufactured by Wright Inc.), porous ceramics, or other biocompatible porous materials allowing for tissue in-growth may be utilized in conjunction with the present invention.

More particularly, and with reference to FIGS. 1 and 3, the interference expansion bolt 10 includes a conical central screw 12 surrounded by a plurality of arcuate shaped expansion members 14 that widen as the expansion bolt 10 is driven (that is, screwed) forward within the expansion members 14. The central screw 12 is provided with a smooth tunnel 16 that allows the addition of a suture 18 to the expansion bolt 10. In accordance with a preferred embodiment, the smooth tunnel, or suture attachment loop, 16 is placed centrally in the hollow core of the present expansion bolt 10, preferably through a fenestration in the conical central screw 12. In accordance with an alternate embodiment, and as discussed below with other embodiments disclosed herein, the suture attachment loop may be a loop affixed to the expansion members or other components of the expansion bolt.

The exterior of the expansion bolt 10, that is, the expansion shell 20, which is composed of the plurality of expansion members 14, is substantially cylindrical with a central aperture 21 in which the central screw 12 is positioned for movement relative to the expansion shell 20 as the central screw 12 is screwed downwardly within the central aperture 21. The expansion shell 20, and consequently the expansion members 14, is made of a porous material, such as a TRABECULAR metal, and is constrained by a lattice structure 28. It is contemplated the lattice structure 28 will take the form of a net-like circumferential web. Preferably, the web is composed of a coiled spring 28 which wraps about the expansion members 14 in a manner holding them circumferentially about the central screw 12 while permitting outward expansion as described below in greater detail. In accordance with a preferred embodiment, the lattice structure 28 is formed from the same material as the expansion members 14. It is contemplated other lattice structures may be employed without departing from the spirit of the present invention so long as the lattice structure allows for expansion and contraction under the hoop forces to allow the expansion bolt to get bigger and smaller.

As discussed above, the expansion bolt 10 functions by (1) first being deployed into the target area in its small diameter form and (2) progressively expanding the expansion shell 20 from a small first diameter to a larger second diameter until the appropriate amount of "hoop stress" pressure is placed for optimal tissue in-growth and frictional engagement of the expansion bolt within the target area. In addition to enhancing tissue in-growth as discussed above, it has been found the applied pressure produces ideal tendon in-growth when the pressure is re-applied after allowing one minute of intervening creep of the viscoelastic tissue as it is held in position by the expansion bolt 10. This can be controlled by a torque wrench 53 with a tapping head 55 to achieve rapid, biologic tissue in-growth formation. Once properly deployed in accordance with the present invention, the interference expansion bolt 10 is preferably left in place for tissue regeneration.

More particularly, the expansion bolt 10 includes a conical central screw 12 about which the expansion shell 20 is positioned. The central screw 12 includes a first end 22 and a second end 24. The central screw 12 is preferably manufactured from biocompatible materials offering durability and ease of manufacture and use. The first end 22 is provided with an enlarged head 26 which is shaped and dimensioned for engagement with a torquing tool, for example, a torque wrench 53, for rotation of the central screw 12 in a manner securing the expansion bolt 10 to the bone and expansion of the expansion shell 20. The central screw 12 extends along the center of the expansion bolt 10 and the expansion shell 20 composed of the plurality of expansion members 14 which extend about the central screw 12. The expansion members 14 are securely held in a position about the central screw 12 by the lattice structure 28 that holds the various expansion members 14 in position, while allowing for expansion of the expansion shell 20 as described herein. The lattice structure 28 is held in position on the expansion shell 20 by a circumferential groove 29 formed in the expansion shell 20, wherein the lattice structure 28 is seated within the circumferential groove 29 preventing movement of the lattice structure 28 along the length of the expansion shell 20.

As briefly discussed above, the expansion members 14 are porous and are preferably composed of elemental metal tantalum fabricated with interconnected porosity through the use of a metal vapor deposition technique. However, and as also discussed above, it is contemplated that porous titanium, porous cobalt chrome, porous aluminum, porous stainless steel or other biocompatible porous materials allowing for tissue in-growth may be utilized in conjunction with the present invention. As discussed above, the central screw 12 may be composed of a variety of biocompatible materials. It is contemplated the central screw 12 may also be manufactured from the same porous materials as those from which the expansion members 14 are constructed. By constructing the central screw 12 and the expansion members 14 from the same material, galvanic corrosion will be decreased.

Expansion of the expansion shell 20 from a first diameter to a larger second diameter as the central screw 12 is screwed into the underlying bone, is achieved by providing the bolt (or screw) body 30 of the central screw 12 with an outer camming surface 32 which increases in diameter as it extends from the second end 24 of the central screw 12 to the first end 22 of the central screw 12. The expansion members 14 are similarly provided with an inner camming surface 38 that rides over the outer camming surface 32 such that as the central screw 12 is drawn further into the expansion shell 20, the larger diameter portion 40 of the bolt body 30 engages the respective inner camming surfaces 38 of the expansion members 14 forcing the expansion members 14 outwardly such that their respective outer surfaces 42 engage the bone in a manner discussed below in greater detail. The outer camming surface 32 and inner camming surfaces 38 are preferably fabricated or post fabrication manipulated (machined) so as to achieve a high coefficient of friction—between 0.5 and 2.0 (ideally 1.0) for holding the central screw 12 relative to the expansion shell 20.

In practice, and with reference to FIGS. 4A, 4B, 4C and 4D, the present expansion bolt 10 is installed in the following manner. First, the bone structure 44 is predrilled. The bone structure 44 is predrilled creating a cavity 46 with a diameter sufficient to accommodate the insertion of the expansion bolt 10 with the outer surfaces 42 of the expansion members 14 adjacent to but not in contact with the inner surface 48 of the cavity 46 formed by the drill (see FIG. 4A). The tendon 50, or other tissue (for example, ligament), is positioned within the cavity 46 formed by the drilling of the bone structure 44 (see FIG. 4B). Alternatively, the tendon 50 may be positioned and tensioned to the various attachment points within and on each major subcomponent thereof which allow the addition of a suture of the expansion bolt 10. The expansion bolt 10 is inserted in the cavity 46 with the tendon 50 between the expansion bolt 10 and the inner surface 48 of the cavity 46 and lightly tapped (that is, hammered) into place using the tapping head 55 of the torque wrench 53. The central screw 12 is then screwed downwardly within the expansion shell 20 using a torque wrench 53 to set the interference expansion bolt 10 in a desired position (see FIG. 4C). The downward movement of the central screw 12 causes the outer camming surface 32 of the central screw 12 to engage the respective inner camming surfaces 38 of the expansion members 14 in a manner pushing the expansion members 14 outwardly and into contact with the tendon 50; pressing the tendon 50 between the wall of the cavity 46 and the expansion members 14 (see FIG. 4D). In addition to the frictional interaction between the tendon 50, bone 44 and expansion bolt 10, the porous construction of the expansion members 14 stimulates tissue in-growth and healing which ultimately leads to a more secure coupling of the tendon 50 to the bone 44.

The expandable nature of the present expansion bolt 10 also allows one implant to function over a range of implant sizes. In accordance with a preferred embodiment, the diameter of the expansion shell 20 is expanded within the limits of the constraining lattice structure 28 allowing the expansion bolt 10 to enlarge and fill a predetermined area. It is contemplated it may be desirable to add a groove to the expansion bolt to accommodate large tendon grafts.

In addition to the biotendoesis procedure described above, the present porous interference expansion bolt 10 has a number of surgical applications. Although these procedures are described herein with reference to the embodiment disclosed in FIGS. 1 to 3, these procedures may also be performed using the embodiments described below.

For example, and with reference to FIGS. 5A, 5B, 5C and 5D, the expansion bolt 10 can be used as an arthroereisis implant relying on soft-tissue integration for fixation. In particular, the present expansion bolt 10 is inserted below the talus 51 (see FIG. 5A). Insertion of the expansion bolt 10 is preferably achieved through the use of a guide rod. Once the expansion bolt 10 is positioned within the talus 51, imaging is employed to confirm proper placement of the expansion bolt as shown with reference to FIGS. 5B and 5C (for example, that the expansion bolt 10 is inserted to the midline of the talus 51). Thereafter, a torque wrench 53 is used to expand the expansion bolt 10 so as to block eversion (see FIG. 5D). Once expanded in position, the expansion bolt 10 is retained under the talus 51 allowing tissue in-growth (which will take 3 to 6 weeks). In this way, no trial components are required, operative time is decreased, tissue manipulation is minimized, and implant inventory is reduced as the expansion bolt 10 may function over a wide and variable expansion size.

In another example, the porous interference expansion bolt 10 can be used as a suture anchor. The porous interference expansion bolt 10 has a suture (or plurality of tissue affixing materials: for example, endobuttons) secured 18 to one side. A cavity 46 is prepared in the bone 44 and the porous metal expansion bolt 10 is deployed within the bone 44. Bone grows into the bolt's surface providing secure fixation for the suture 18 and allows the construct to function as a suture anchor with the suture type left to the surgeon's preference. The use of the expansion bolt 10 as a suture anchor is achieved using conventional suture anchor techniques. Briefly, and as will be described below in greater detail, the expansion bolt 10 is secured to the bone structure 44 and a suture 18 is either preattached to the expansion bolt 10 or the suture 18 is attached to the expansion bolt 10 after its attachment to the bone structure 44. After the expansion bolt 10 is fixedly secured to the bone structure 44, the free end of the suture 18 is placed into soft tissue 50 and the soft tissue 50 is pulled to the bone 44 by means of the suture-expansion bolt attachment. By employing the present expansion bolt 10 as suture anchor, one may draw soft tissue 50 to the bone structure 44 while similarly getting bone in-growth and potentially surface soft-tissue in-growth. Referring to FIGS. 6A, 6B, 6C and 6D, the suture anchoring technique in accordance with a preferred embodiment of the present invention is achieved by first predrilling the bone structure 44. The bone structure 44 is predrilled creating a cavity 46 with a diameter sufficient to accommodate the insertion of the expansion bolt 10 with the outer surfaces 42 of the expansion members 14 adjacent to, but not in contact with, the inner surface 48 of the cavity 46 formed by the drill (see FIG. 6A). The expansion bolt 10 with a suture 18 secured thereto is positioned within the cavity 46 formed by the drilling of the bone structure 44 (see FIG. 6B) and lightly tapped (that is, hammered) into place using the tapping head 55 of the torque wrench 53. The central screw 12 is then screwed downwardly within the expansion shell 20 using a torque wrench 53 to set the interference expansion bolt 10 in a desired position. The downward movement of the central screw 12 causes the outer camming surface 32 of the central screw 12 to engage the respective inner camming surfaces 38 of the expansion members 14 in a manner pushing the expansion members 14 outwardly and into contact with the inner surface 48 of the cavity 46 frictionally holding the expansion bolt 10 in position within the cavity 46 (see FIG. 6C). The suture 18 is then tied (or otherwise coupled) to tissue (for example, ligament or tendon) 50 in a manner anchoring the tissue 50 relative to the expansion bolt 10 (see FIG. 6D). The porous construction of the expansion members 14 stimulates tissue in-growth that ultimately leads to a more secure coupling of the expansion bolt 10 to the bone 44.

In yet another example, the porous interference expansion bolt 10 can be used as a bone void filler. Referring to FIGS. 7A, 7B, 7C and 7D, the porous interference expansion bolt 10 is placed within an area for bony fusion or an area where space needs to be filled with a structurally competent substance, for example, within a joint 45 requiring fusion (the subtalar joint as shown in the disclosed example). First the joint 45 is drilled across the bone structures 44a, 44b creating a cavity 46 composed of first and second cavity member 46a, 46b (see FIGS. 7A and 7B). The expansion bolt 10 is then inserted across the bone structures 44a, 44b and within the cavity 46 (see FIG.

Figure 7A:
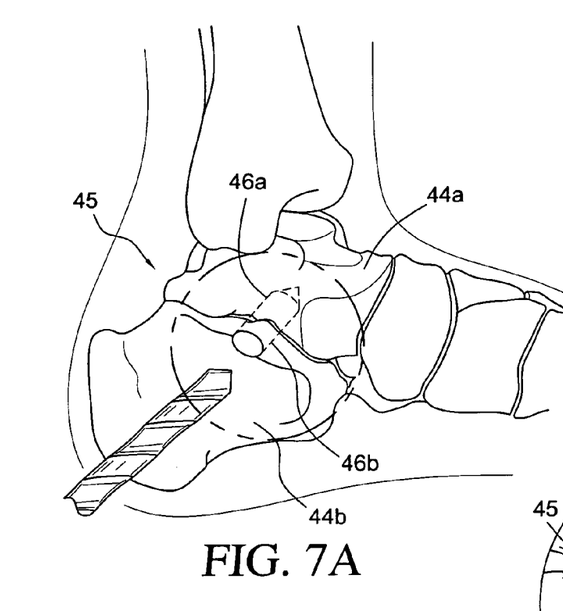
FIGS. 7A-D show the step of using the expansion bolt shown in FIGS. 1-3 in a bone fusion procedure.
Figure 7B:
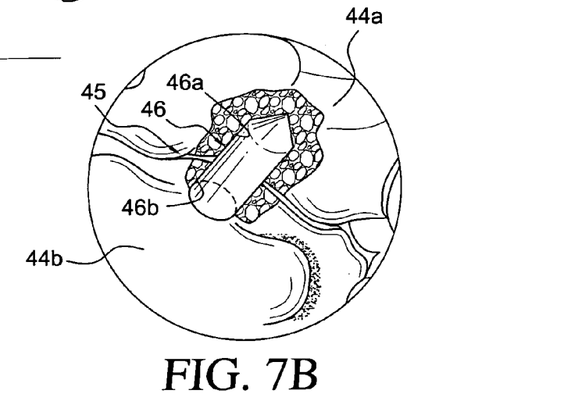
Figure 7C:
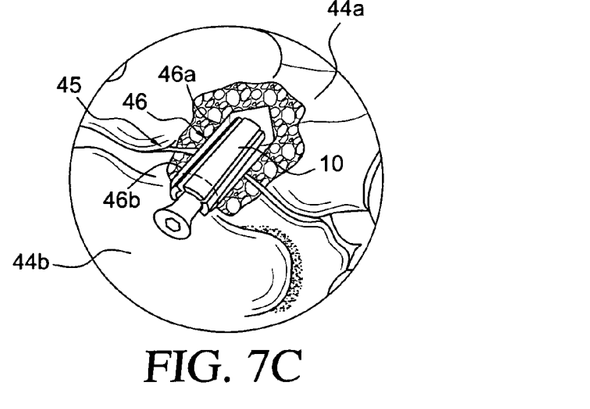
Figure 7D:
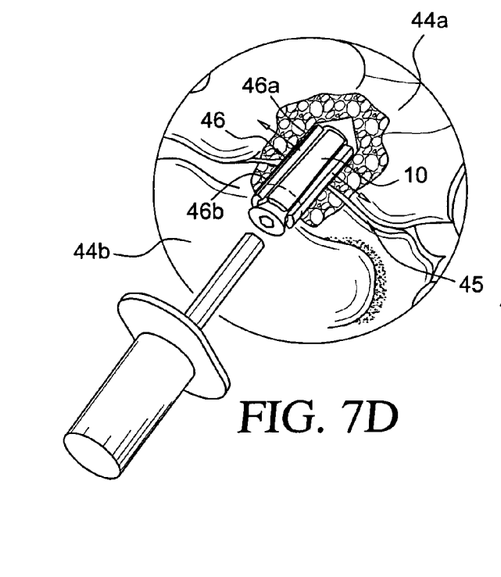

7C). The expansion bolt 10 is then expanded (for example, using a torque wrench 53) to secure it in position (see FIG. 7D). Expansion causes secure fixation, as well tissue ingrowth stimulating bone healing and void filling. This could be used in intramedullary, first metatarsal phalangeal, subtalar and ankle fusion, soft-tissue as well as other orthopedic areas.

Referring to FIGS. 8, 9, 10A, 10B, 10C and 10D, another preferred embodiment of the present surgical expansion bolt 110 is disclosed. As shown with reference to the attached drawings, the surgical expansion bolt 110 includes a threaded central screw 112 shaped and dimensioned to fit within a central aperture 121 of an expansion shell 120 for acting upon the expansion shell 120 in a manner causing controlled outward expansion thereof. As with the embodiment disclosed above with reference to FIGS. 1 to 3, the central screw 112 is provided with a smooth tunnel (or suture attachment loop) 116a, 116b, 116c that allows the addition of a suture 118 to the expansion bolt 110. In accordance with a preferred embodiment, the smooth tunnel, or suture attachment loop, 116a, 116b, 116c may be formed through the enlarged head 126 of the central screw 112, directly on expansion shell 120 or in the nut 162 (discussed below).

Figures 8, 8A, 8B:
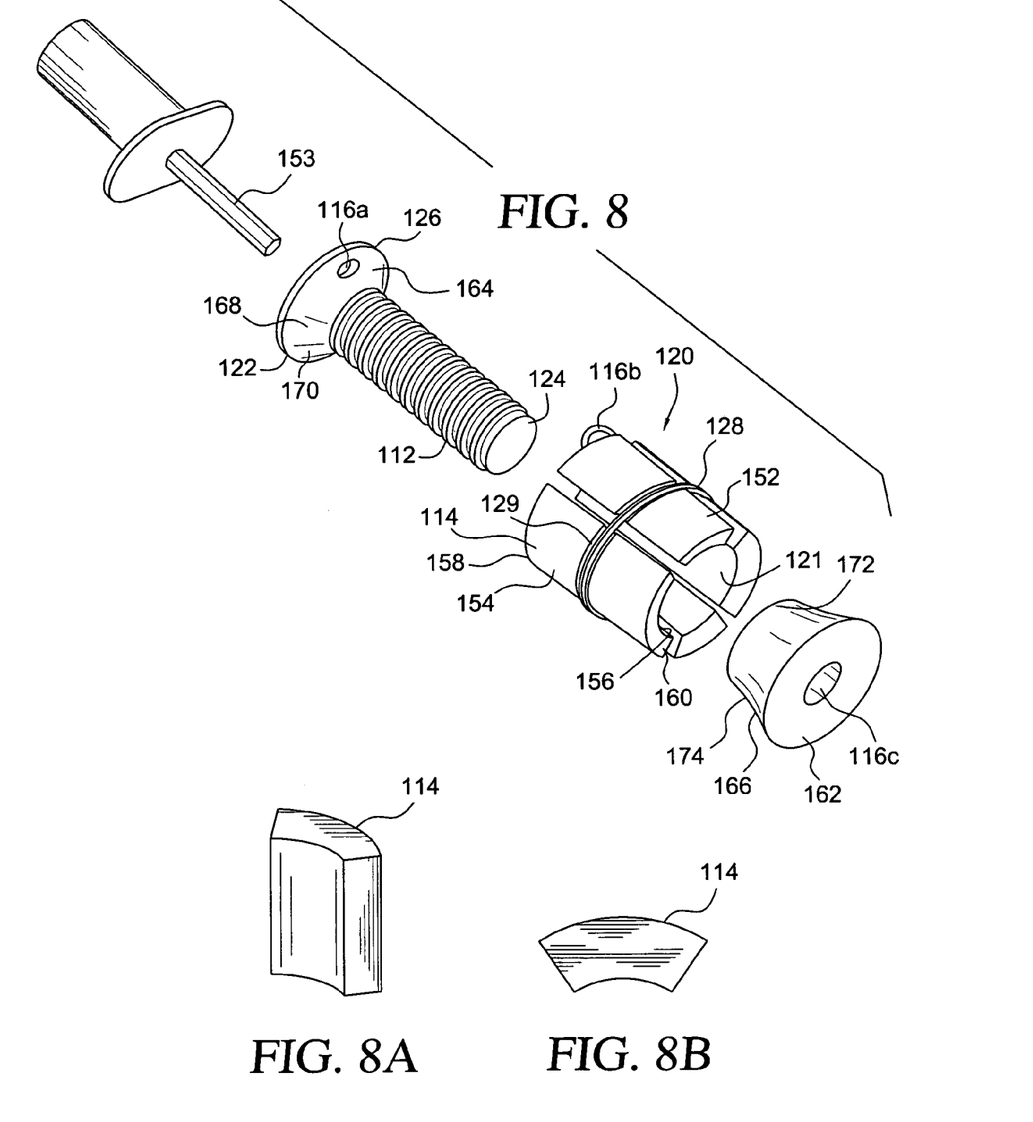
FIG. 8 is an exploded view of an expansion bolt in accordance with an alternate embodiment.
FIG. 8A is a perspective view of an expansion member and FIG. 8B is a side plan view of an expansion member.
Figure 9:
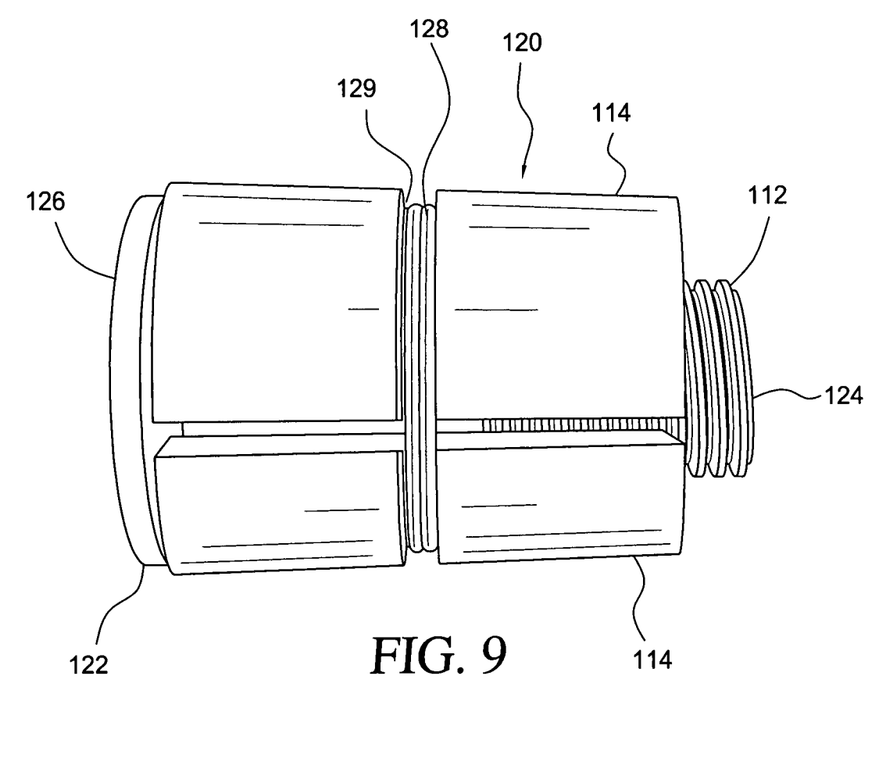
FIG. 9 is a top plan view of the expansion bolt (without the conical nut) shown in FIG. 8.

In accordance with this embodiment, the expansion shell 120 is a porous metal wedge 152 composed of a plurality of expansion members 114 held together via a lattice structure 128. The expansion shell 120 is substantially annular in shape and includes an outer surface 154 and inner surface 156, as well as a first end 158 and second end 160. The wedge 152 is formed such that when compressive forces are applied to both the first end 158 and the second end 160 thereof, the diameter of the outer surface 154 of the wedge 152 will increase as the expansion members 114 of the porous metal wedge 152 are pushed apart.

As briefly discussed above, the expansion shell 120 is porous and is composed of elemental metal tantalum fabricated with interconnected porosity with use of a metal vapor deposition technique. However, it is contemplated that porous titanium, porous cobalt chrome, porous aluminum, porous stainless steel or other biocompatible porous materials allowing for tissue in-growth may be utilized in conjunction with the present invention.

More particularly, the surgical expansion bolt 110 includes a central screw 112 having a first end 122 with an enlarged head 126 and a second end 124 to which a conical nut 162 is secured. Between the enlarged head 126 and the nut 162, the expansion shell 120 is positioned. The expansion shell 120 is substantially cylindrical and includes a central aperture 121 shaped and dimensioned for the passage of the central screw 112 therethrough. The expansion shell 120 is composed of a plurality of expansion members 114 secured together via a lattice structure 128 in a manner allowing for expansion thereof. It is contemplated the lattice structure 128 will take the form of a net-like circumferential web. Preferably, the web is composed of a coiled spring 128 which wraps about the expansion shell 120 in a manner holding it circumferentially about the central screw 112 while permitting outward expansion. In accordance with a preferred embodiment, the lattice structure 128 is formed from the same material as the expansion shell 120 and is seated within a circumferential groove 129 formed in the expansion shell 120. It is contemplated other lattice structures may be employed without departing from the spirit of the present invention so long as the lattice structure allows for expansion and contraction under the hoop forces to allow the expansion bolt to get bigger and smaller.

The first and second ends 158, 160 of the expansion shell 120 are respectively formed with first and second inwardly tapered camming surface 164, 166. The first and second inwardly facing tapered camming surface 164, 166 are respectively shaped and dimensioned to interact with a first outwardly facing tapered camming surface 168 formed along the bottom surface 170 of the enlarged head 126 of the central screw 112 and a second outwardly facing tapered camming surface 172 formed along the upper surface 174 of the nut 162.

Figure 10A:
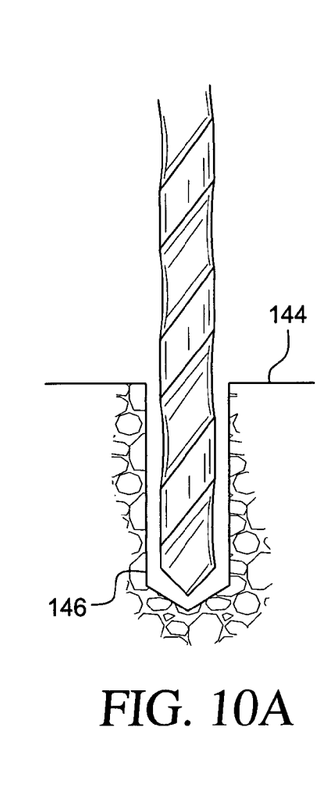
FIGS. 10A-D show the steps in using the expansion bolt shown in FIGS. 8 and 9 for securing a ligament.
Figure 10B:
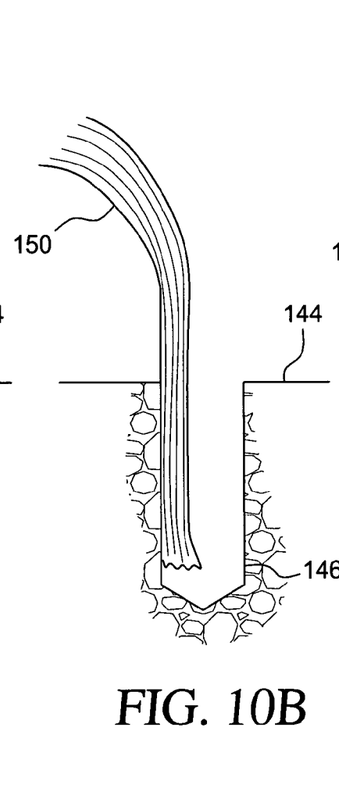
Figure 10C:
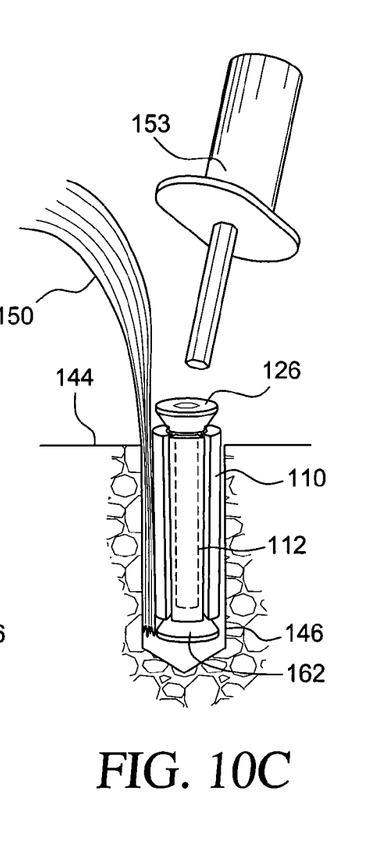
Figure 10D:
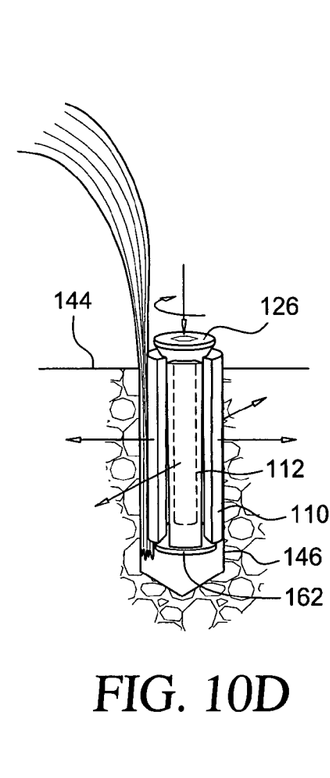

In practice, and with reference to FIGS. 10A, 10B, 10C and 10D, a cavity 146 is first formed within the bone 144 utilizing a conventional bone drill (see FIG. 10A). Thereafter, a ligament 150, or other tissue (for example, tendon), is positioned within the cavity 146 such that the ligament 150 is held in a facing relationship with the sidewall of the cavity 146 formed via the drill (see FIG. 10B). Thereafter, the surgical expansion bolt 110 is placed within the cavity 146 in its compressed orientation and lightly tapped into position. The central screw 112 is then screwed down using a torque wrench 153 such that the enlarged head 126 of the central screw 112 is drawn toward the internally threaded nut 162 threaded onto the distal (or second) end 124 of the central screw 112 (see FIG. 10C). In accordance with a preferred embodiment, the frictional interaction between the nut 162 and the expansion members 114 allows rotation of the central screw 112 relative to the nut 162 for drawing the nut 162 up the central screw 112 in a manner expanding the expansion members 114. However, it is contemplated flutes or guide ridges for engaging the wall of the cavity 146 may be formed along the nut 162 to keep the nut 162 in rotational alignment while allowing axial movement (compression) of the nut 162 relative to the central screw 112. As the central screw 112 is screwed into the nut 162, the enlarged head 126 and nut 162 are drawn together in a manner compressing the expansion shell 120 and causing the respective camming surfaces 164, 166, 168, 172 of the expansion shell 120, enlarged head 126 and nut 162 to act upon one another in a manner causing the expansion shell 120 to expand outwardly and into contact with the ligament 150. With the ligament 150 pressed against the bone 144 and between the porous expansion shell 120, tissue in-growth is permitted between the bone 144, ligament 150 and porous expansion shell 120 (see FIG. 10D). In this way, a secure attachment of the ligament 150 to the underlying bone 144 is achieved in a desirable and highly efficient manner.

As those skilled in the art will certainly appreciate, other possible constructions are possible for attachment of the bolt to the bone structure. For example, and with reference to FIG. 11, an anchor 276 may be formed with a helical, corkscrew like anchor member 278 that is screwed into a bone structure (for example, using a handheld driving device 253) for anchoring of a tendon thereto. With the anchor 276 securely mounted within the bone, a bolt 280 and washer 282 may be secured to the anchor 276 to fixedly couple a tendon, ligament, or other tissue thereto.

Figure 11:
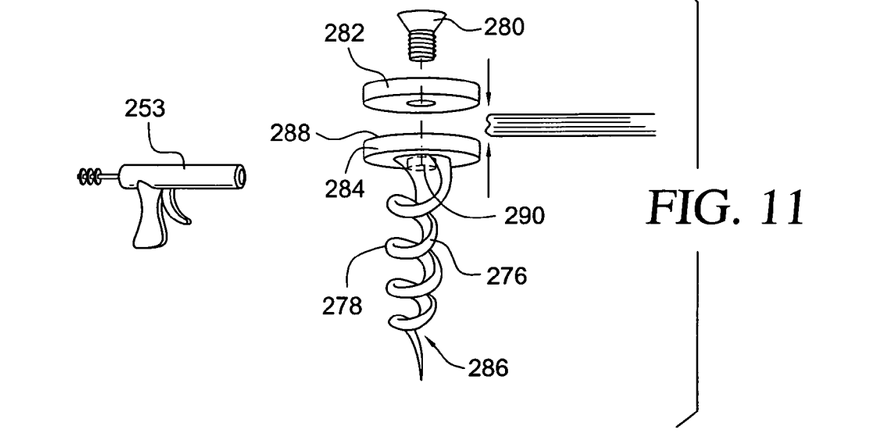
FIGS. 11, 12, 13, 14, 15 and 16 present alternate embodiments in accordance with the present invention.

As such, the anchor 276 includes a first end 284 and a second end 286. As described above, the second end 286 includes the anchor member 278 shaped and dimensioned for mounting within the bone. The first end 284 is provided with a head member 288 having an internally threaded aperture 290 shaped and dimensioned for receiving a similarly threaded bolt 280. In practice, a tendon/ligament is positioned over an implanted anchor 276. Thereafter, a porous washer 282 is positioned on top of the ligament and the ligament is compressed between the first end 284 of the anchor 276 and the washer 282 through the application of force securing the bolt 280 to the anchor 276 with the tendon positioned between the first end 284 of the anchor 276 and the washer 282.

Figure 12:
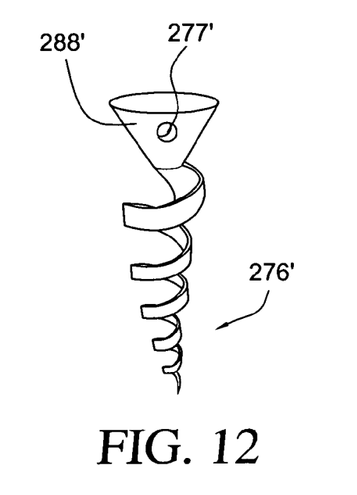

In accordance with an alternate embodiment, and with reference to FIG. 12, the head 288' of the anchor 276' may be formed with an aperture 277' through which a tendon may be pulled.

As with the prior embodiments porous metals are incorporated into the present device to enhance tissue in-growth thereby improving the attachment of the tissue to the underlying bone. As such, the head member 288 of the anchor 276 and the washer 282 are formed of elemental metal tantalum fabricated with interconnected porosity with use of a metal vapor deposition technique. However, it is contemplated that porous titanium, porous cobalt chrome, porous aluminum, porous stainless steel or other biocompatible porous materials allowing for tissue in-growth may be utilized in conjunction with the present invention.

Figure 13:
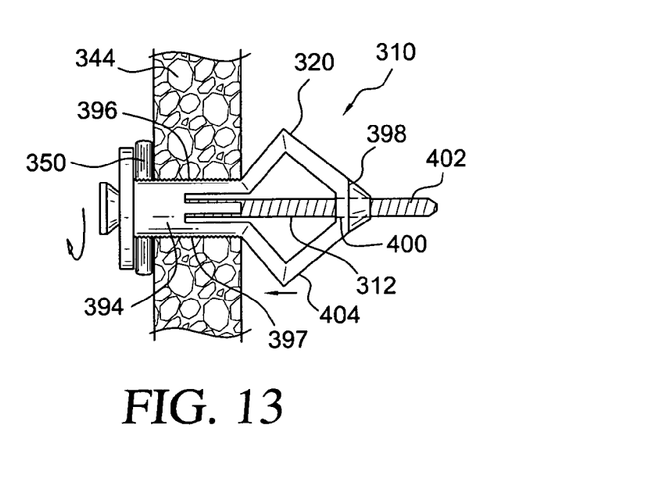
Figure 14:
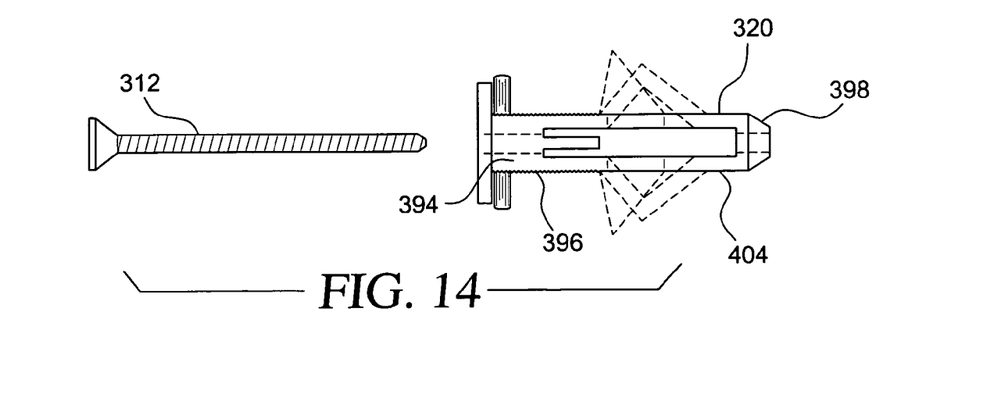

Similarly, and with reference to FIGS. 13 and 14, the expansion bolt 310 may be formed with a threaded central screw 312 that acts upon a porous expansion member 392 to secure tissue to bone. Such an expansion screw is shown in U.S. Pat. No. 3,174,387, which is incorporated herein by reference.

Briefly, the expansion bolt 310 is particularly adapted for securing tissue to the outer surface of a bone 344 where the expansion bolt 310 completely penetrates the bone 344. The expansion bolt 310 includes a central screw 312 having an expansion shell 320 secured thereabout. The expansion shell 320 includes a first tubular section 394. The outer surface 396 of the first tubular section 394 is preferably provided with radially outwardly extending rotation preventing teeth 397 adapted to penetrate into the bone 344 and hold the expansion shell 320 against angular movement as the central screw 312 is rotated. The expansion bolt 310 further includes a second tubular section 398 which is formed with a cylindrical peripheral surface having a diameter less than the diameter of the aperture to be formed by the bone drill forming a cavity within the bone 344 such that the second tubular section 398 may be passed through the aperture caused by the bone drill. It will be noted that the two tubular sections 394, 398 are coaxial and that the second tubular section 398 is provided with internal threads 400 adapted to mesh with the external threads 402 of the central screw 312 that is introduced through the tissue and through the aperture of the first tubular section 394. The first and second tubular sections 394, 398 are connected by respective end portions of elongated ribs 404 that are deformable radially outwardly with respect to the axis of the expansion bolt 310. The ribs 404 are shaped and dimensioned for ready deformation radially outwardly when the central screw 312 is driven home, that is, when the central screw 312 is rotated to move the second tubular section 398 toward the first tubular section 394 whereby the median portions of the ribs 404 are expanded and deformed all the way out into actual abutment with the inner side of the bone 344 to thereby prevent axial displacement of the expansion bolt 310 in an upward direction and pull the tissue 350 held by the expansion bolt 310 into contact with the bone 344.

Figure 15:
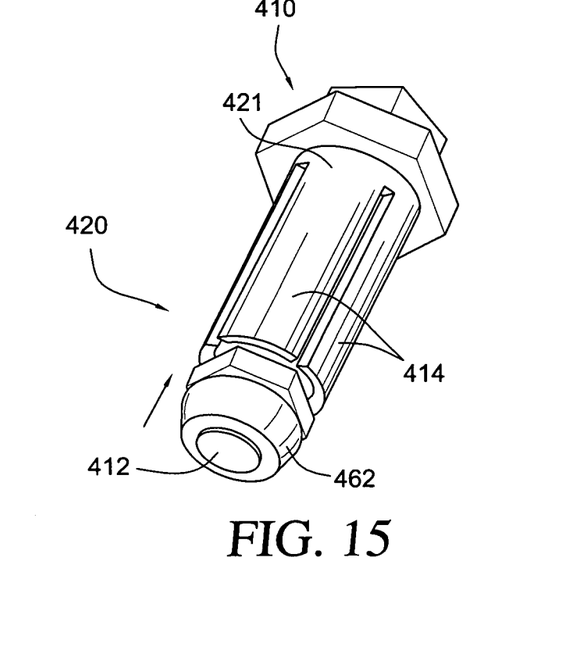
Figure 16:
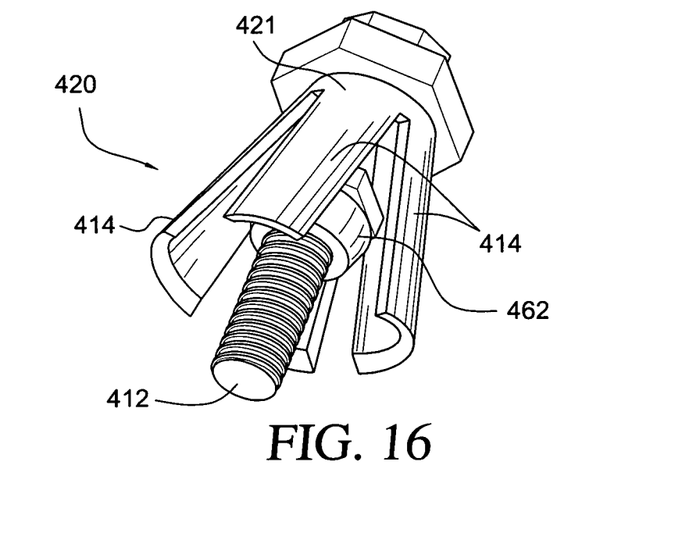

Referring to FIGS. 15 and 16, yet another expansion bolt 410 for use in accordance with the present invention is disclosed. The expansion bolt 410 includes a threaded central screw 412 surrounded by a plurality of expansion members 414 that widen as the expansion bolt 10 is rotated to draw a nut 462 between the expansion members 414 in a manner expanding them outwardly. The exterior of the expansion bolt 410, that is, the expansion shell 420, which is composed of the plurality of expansion members 414, is made of a porous material, such as a TRABECULAR, foam, or porous metal.

The expansion members 414 are held about the screw 412 by an upper ring 421 from which the expansion members 414 extend.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A biocompatible expansion bolt, comprising:
a one-piece central screw including a first end with an integrally formed enlarged screw head having a driving recess and a second end to which a conical nut is secured; and
an expansion shell positioned about the central screw, the expansion shell being substantially cylindrical with a central aperture in which the central screw is positioned for movement relative to the expansion shell and shaped and dimensioned for controlled expansion between a first diameter and a larger, second diameter for applying a predetermined hoop stress optimizing tissue in-growth, wherein the expansion shell is composed of porous material allowing for tissue in-growth, the expansion shell being composed of a plurality of arcuate shaped expansion members solely constrained by a spring lattice structure, the expansion shell including a circumferential groove in which the lattice structure is positioned, the groove having a substantially circular cross section in a plane perpendicular to a longitudinal axis of the expansion shell;
the first end of the central screw includes a first outwardly facing tapered camming surface formed along a bottom surface of the enlarged screw head and the conical nut includes a second outwardly facing tapered camming surface formed along an upper surface of the conical nut, whereby the first outwardly facing tapered camming surface and the second outwardly facing tapered camming surface interact with the expansion shell to control expansion thereof; and
wherein when compressive forces are respectively applied to a first end and a second end of the expansion shell by the first outwardly facing tapered camming surface and the second outwardly facing tapered camming surface, the diameter of an outer surface of the expansion shell will increase along an entire length of the expansion shell as the expansion members of the expansion shell are pushed apart.

2. The expansion bolt according to claim 1, wherein the porous material is elemental metal tantalum.

3. The expansion bolt according to claim 1, wherein the porous material is selected from the group consisting of elemental metal tantalum, porous titanium, porous cobalt chrome, porous aluminum, porous stainless steel, and porous ceramics.

4. The expansion bolt according to claim 1, further including a suture attachment loop.

5. The expansion bolt according to claim 4, wherein the central screw includes the suture attachment loop.

6. The expansion bolt according to claim 4, wherein the expansion shell includes the suture attachment loop.

7. The expansion bolt according to claim 1, wherein the lattice structure is a coiled spring.

8. The expansion bolt according to claim 1, wherein the plurality of expansion members extend along a plurality of different axes.

* * * * *